United States Patent [19]
Keller et al.

[11] Patent Number: 5,891,465
[45] Date of Patent: Apr. 6, 1999

[54] DELIVERY OF BIOLOGICALLY ACTIVE MATERIAL IN A LIPOSOMAL FORMULATION FOR ADMINISTRATION INTO THE MOUTH

[75] Inventors: Brian C. Keller, Antioch; Daniel L. Fisher, Pleasant Hill; Steven Kiss, Pittsburg, all of Calif.

[73] Assignee: BioZone Laboratories, Inc., Pittsburgh, Calif.

[21] Appl. No.: 645,894

[22] Filed: May 14, 1996

[51] Int. Cl.$^6$ .............................. A61K 9/127; A61K 9/12
[52] U.S. Cl. .............................. 424/450; 424/43; 424/45; 424/195.1
[58] Field of Search .............................. 424/450, 43, 45, 424/195.1

[56] References Cited

U.S. PATENT DOCUMENTS

| | | | |
|---|---|---|---|
| 4,525,341 | 6/1985 | Deihl . | |
| 4,636,381 | 1/1987 | Takada | 424/38 |
| 4,839,175 | 6/1989 | Guo | 424/450 |
| 4,892,883 | 1/1990 | Chatterjee et al. | 514/464 |
| 4,897,269 | 1/1990 | Mezei . | |
| 4,916,118 | 4/1990 | Fidler et al. . | |
| 4,937,078 | 6/1990 | Mezei et al. . | |
| 4,983,397 | 1/1991 | Schroit et al. . | |
| 5,043,323 | 8/1991 | Bombardelli et al. | 514/25 |
| 5,049,389 | 9/1991 | Radhakrishnan | 424/450 |
| 5,296,224 | 3/1994 | Schwabe | 424/195.1 |
| 5,378,709 | 1/1995 | Manning et al. . | |
| 5,399,348 | 3/1995 | Schwabe | 424/195.1 |
| 5,451,408 | 9/1995 | Mezei et al. . | |
| 5,468,753 | 11/1995 | Coude et al. . | |
| 5,490,985 | 2/1996 | Wallach et al. . | |
| 5,591,768 | 1/1997 | Lewy | 514/415 |
| 5,653,996 | 8/1997 | Hsu | 424/450 |

OTHER PUBLICATIONS

Rowland and Tozer, "Clinical Pharmacokinetics: Concepts and Applications" (1980) pp. 16–31.

Mutschler and Derendorf, "Drug Actions: Basic Principles and Therapeutic Aspect," (English Ed. 1995), pp. 11–26.

Goodman and Gilman, *Liposome Technology*, 2nd ed., Chapter 3, "Liposome Preparation Using High–Pressure Homogenizers," vol. 1, pp. 49–65 (1993), CRC Press, Boca Raton, Florida.

Goodman and Gilman, *Liposome Technology*, 2nd ed., Chapter 4, "Preparation of Large Unilamellar Liposomes With High Entrapment Yield by Rotary Dialysis or Agarose Plug Diffusion," vol. 1, pp. 67–79 (1993), CRC Press, Boca Raon, Florida.

Goodman and Gilman, *Liposome Technology*, 2nd ed., Chapter 5, "A Mild Method for the Preparation of very Large Unilamellar Liposomes," vol. 1, pp. 81–97 91993), CRC Press, Boca Raton, Florida.

Goodman and Gilman, *Liposome Technology*, 2nd ed., Chapter 6, "Preparation of MLV by the Rev Method: Vesicle Structure and Optimum Solute Entrapment," vol. 1, pp. 99–109 (1993), CRC Press, Boca Raton, Florida.

Goodman and Gilman, *Liposome Technology*, 2nd ed., Chapter 7, "Production and Size Control of Large Unilamellar Liposomes by Emulsification," vol. 1, pp. 111–121 (1993), CRC Press, Boca Raton, Florida.

Goodman and Gilman, *Liposome Technology*, 2nd ed., Chapter 8, "Reduction of Liposome Size and Preparation of Unilamellar Vesicles by Extrusion Techniques," vol. 1, pp. 123–1349 (1993), CRC Press, Boca Raton, Florida.

Lee Essential oils, cosmetics 112, p. 381 # 204476a, 1990.

*Primary Examiner*—Gollamudi S. Kishore
*Attorney, Agent, or Firm*—Morrison & Foerster LLP

[57] ABSTRACT

The present invention provides compositions and methods of administering nutritional supplements. The compositions and methods of the present invention are based on nutritional supplements that are encapsulated in lipid vesicles for administration as an aerosol or liquid droplet spray.

**9 Claims, No Drawings

DELIVERY OF BIOLOGICALLY ACTIVE MATERIAL IN A LIPOSOMAL FORMULATION FOR ADMINISTRATION INTO THE MOUTH

TECHNICAL FIELD

The invention relates to the field of orally or nasally administered nutritional supplements, particularly herbs and plant extracts as well as orally or nasally administered pharmacologically active agents, particularly drugs. The invention specifically relates to formulations and methods for the delivery of aerosol or spray compositions comprising lipid encapsulated drugs or nutritional supplements that can be absorbed sublingually, particularly under the tongue and between the cheek and gum or can be administered nasally for local or systemic action.

BACKGROUND ART

Nutritional supplements and pharmaceutical agents are typically provided in solid dosage formulations that are taken orally. Examples of solid dosage forms include coated tablets, compressed tablets, compressed capsules and two piece gelatin capsules. Such forms have the advantage of being easy and relatively inexpensive to produce, readily dispensable, and fairly stable. Dosage form is an important factor that influences the absorption and bioavailability of a compound.

Solid dosage formulations of drugs and nutritional supplements have the disadvantage that many of the ingredients in the supplement are degraded by stomach acids. Degradation within the stomach serves to decrease the therapeutic response to orally administered solid agents. Degradation can be an important factor which limits the effectiveness of drugs and nutritional supplements, such as plant extracts, which are taken for medicinal purposes.

Another disadvantage to solid dosage forms is that a fraction of the population is either unable to swallow the solid form or are reluctant to take such "pills." Further, the gag reflex action provides a barrier to tablet size. As the size of the solid form increases, the percentage of people who will have trouble swallowing the solid form also increases. This problem becomes particularly acute when high dosages are required to overcome degradation such as with the administration of many pharmaceutical agents and nutritional supplements taken for medical or other purposes.

The activity of a substance that is administered into the mouth is largely dependent on the amount of the substance that reaches the bloodstream and the rate at which it reaches the bloodstream. By increasing the rate and extent of absorption, the activity of the substance can be enhanced, therefore reducing the amount needed in the oral formulation. It has become increasingly important in the area of substance delivery, and in the treatment of any disease or disorder, to increase the availability of the substance. However, in general, this focus has not been applied to nutritional supplements.

The term availability is used to indicate the completeness of absorption. The term bioavailability is a term for the clinical description of availability in vivo and indicates the extent to which a substance reaches the bloodstream. Bioavailability is defined as the fraction or percentage of the administered dose that is ultimately absorbed intact. (Rowland and Tozer, "Clinical Pharmacokinetics: Concepts and Applications," (1980), pp. 16–31.

The rate or speed of absorption and the extent or ratio of the amount of active material absorbed over the amount administered depends on several factors. The most important factors include, 1) dosage form and delivery system, 2) physicochemical properties of the drug, particularly solubility, 3) dose, 4) site of administration, 5) vascularization of the absorption site, 6) contact time with the absorption surface, and 7) pH at the site of absorption. (Mutschler and Derendorf, "Drug Actions: Basic principles And Therapeutic Aspect", (English Ed 1995), pp. 11–26.

Solid dosage forms are absorbed following oral administration by a two-step process. This two-step process can be the rate limiting step in the absorption process that can delay onset of action and slow the therapeutic response by the patient. The two-step process is 1) dissolution of the solid dosage and 2) absorption of drug in solution.

Many compounds that are orally administered are chemically defined as weak acids or weak bases and exist in solution as an equilibrium between the nonionized and the ionized forms. Increased accumulation of compound on the side of membrane whose pH favors a greater ionization of the compound has led to the pH partition hypothesis. According to this hypothesis, only a nonionized nonpolar drug penetrates the membrane, and at equilibrium the concentration of the nonionized species is equal on both sides of the membrane. The nonionized form is assumed to be sufficiently lipophilic to penetrate the membrane. If it is not, there is no absorption, irrespective of pH. The fraction of nonionized compound at the absorption site is controlled by both the pH and pKa of the compound, according to the Henderson-Hasselbalch equation. (Goodman and Gilman's "The Pharmacological Basis of Therapeutics", 9th ed. (1996) pp. 4–22).

The mucosa of the mouth and throat is highly vascularized and well suited for the absorption of lipophilic, nonionized compounds. These routes of absorption are particularly advantageous for compounds that are needed to have a rapid onset of action or are not well absorbed when taken orally. This route of administration circumvents exposure of compounds to digestive enzymes and the high acidity of the gastrointestinal tract that can be damaging to compounds and render them inactive.

Administration by the sublingual or buccal route further avoids the first-pass effect from hepatic enzymes immediately upon absorption. The term first-pass effect is used to characterize the fraction of the drug that is metabolized during the first exposure to the gut wall and the liver. All compounds that are absorbed from the gastrointestinal tract go to the portal vein and the liver before entering the systemic circulation. This means that before a drug that has been absorbed across the membrane of the gastrointestinal mucosa can reach the general circulation it has to pass through the liver.

There are some biologically active compounds that are delivered sublingually to achieve a rapid onset and greater bioavailability. For example, by administering nitroglycerin tablets under the tongue, rapid onset is achieved by virtue of quick absorption into the blood stream through the highly vascularized capillary plexus. In addition this route avoids the liver where the compound is highly metabolized on first exposure to metabolic enzyme systems. Another example of a compound that is administered orally for absorption in the mouth is methyltestosterone. Supplied in tablet form that is designed for absorption through the buccal mucosa into systemic circulation, this route provides twice the androgenic activity of oral tablets. Another approach to the administration of compositions such as vitamins is disclosed in U.S. Pat. No. 4,525,341 to Deihl which involves the production of an aerosol administered with a pulmonifer in the form of a suspension of droplets dispersed in a carrier gas. However, none of the available compositions for oral absorption have been formulated in the form of lipid encapsulation.

A variety of liposomal products are known that enhance uptake or facilitate delivery of various products. For example, the parenteral and topical uses of liposomal carriers were reported to protect a drug against hostile environments and to provide controlled release of the drug while circulating in the blood or after immobilization at a target tissue such as the skin. "Liposome Technology", 2nd Ed, Vol. I (1993) G. Gregoriadis ed., CRC Press, Boca Raton, Fla. The topical administration of drugs such as Minoxidil® has been reported by Mezei (U.S. Pat. No. 4,897,269) as well as the pulmonary administration of liposomes-encapsulated opioid analgesic agents (U.S. Pat. No. 5,451,408). Mezei also has reported the use of a topical liposomal local anesthetic product said to be useful in producing local anesthesia of mucous membrane-covered surfaces (U.S. Pat. No. 4,937,078).

Despite the foregoing advantages of sublingual routes of administration and of the use of lipid encapsulation, these two methods have not been combined and applied to drug and nutritional supplement delivery, particularly in an aerosol or spray delivery form. The present invention provides novel delivery systems for administering agents, such as drugs and nutritional supplements, whereby the agent is lipid encapsulated, into lipid vesicles or liposomes, and administered as an aerosol or spray into the mouth for subsequent absorption in the mouth, the throat and/or the gastrointestinal tract. The results provided in the Examples indicate that such lipid encapsulated aerosol or spray formulations provide increases in the bioavailability and improved therapeutic response for a wide variety of pharmacological agents and nutritional supplements.

SUMMARY OF THE INVENTION

The present invention provides formulations of agents, such as drugs, hormones and nutritional supplements, which comprise an aerosol or a spray containing the agent in lipid encapsulated form. The agents of the present invention include purified components such as drugs and purified vitamins or minerals, as well as semi-purified components such as plant extracts.

The lipid encapsulated nutritional supplements of the present invention includes lipid vesicles and/or liposomes comprised of lecithin, ceramides, phosphatidylethanolamine, phosphotidylcholine, phosphatidylserine, cardiolipin and the like. In addition, the compositions of the present invention may include lipid vesicles and/or liposomes of a variety of types, multilamellar vesicles and unilamellar vesicles.

The compositions of the present invention are intended to be formulated for administration as an aerosol or spray using known aerosol or pump spray delivery devices. These include coarse liquid sprays, aerosols of colloidal suspensions of liquid droplets in a gaseous carrier such as oxygen, nitrogen or a hydrocarbon propellant, and temporary suspensions of liquid droplets in the carrier.

The present invention further provides improved methods for administering an agent, such as a drug or a nutritional supplement, to a subject, wherein the improvement comprises orally administering, as an aerosol or spray, a lipid encapsulated agent for subsequent sublingual or buccal adsorption or nasally administering, as an aerosol or spray, a lipid encapsulated agent for subsequent local or system action.

DETAILED DESCRIPTION OF THE PREFERRED EMBODIMENTS

The present invention provides compositions and methods for orally or nasally administering agents such as drugs, hormones and nutritional supplements. Specifically, the present invention provides formulations for orally or nasally administering agents comprising an aerosol or spray containing one or more lipid encapsulated agents. The present invention further provides devices which deliver an oral or nasal aerosol or spray formulation comprising a lipid encapsulated agent. The present invention further provides methods for orally or nasally administering agents wherein one or more agents are lipid encapsulated and supplied as an aerosol or spray into the mouth or into the nasal cavaty respectively. The compositions, devices and methods of the present invention provide improvements over conventional means previously used for the administration of agents such as drugs and nutritional supplements by increasing the rate of absorption and bioavailability of the agent, particularly if administered sublingually, thus increasing effectiveness and perhaps decreasing the amount of agent that is administered.

As used herein, an agent is any biologically active substance which is intended to be administered to a subject. An agent is biologically active when the agent exerts a biological effect when administered to an organism. The agents which can be formulated in the present composition include pharmaceutical agents such as drugs, hormones and nutritional supplements such as plant extracts and vitamins. The most preferred drugs are those requiring rapid onset or sustained blood levels (or both), such as cardiovascular agents and agents which target the central nervous system, in particular, cardiovascular agents like digoxin, amrinone and milrinone; nitrates like amyl nitrite, nitroglycerin, isosorbide dinitrite, isosorbide mononitrite, erythrityl tetranitrate, pentaerythritol tetranitrate; antiarrthymic drugs like moricizine and lidocaine; calcium channel blocking agents like diltiazem and nifedapine; vasopressors like isoproterenol, metaraminol and methoxamine; beta-adrenergic blocking agents like propranolol, metorpolol, acebutolol, timolol busoprolol and esmolol. Other antihypertensives include prazocin, guanadrel sulfate, hydralazine, minoxidil, quinapril, enalapril, losartan potassium, phentolamine, phenoxybenzamine HCl, tolazoline HCl; central nervous system drugs like CNS stimulants like caffeine, analgesics like morphine, oxymorphone, sufentanil citrate, fentanil, alfentanil HCl, hydromorphone, merperidine, butorphanol, nalbuphine, dezocine, acetaminophen, NSAIDS and sumatriptan.; antiemetic/antivertigo agents like chlorpromazine, prochlorpromazine, cyclazine, diphenidol, scopalamine, corticosteroids, cannabinoids, and odansetron HCl; antianxiety agents like benzodiazepines, meprobamate, and buspiron; antidepressants like amitriptyline, amoxapine, venlafaxine, trazodone, and fluoxetine; antipsychotic agents like trifluperazine, thioridazine, trifluodiazepine, loxapine, pimozide, lithium methylphenadate, and dihydrogenated ergot is alkaloids; sedative hypnotics like ethchlorvinyl, chloral hydrate, doxalamine duccinate, diphenhydramine, and phenobarbital; anticonvulsants like phenytoin, valproic acid, methsuxamide, and carbamazepine; muscle relaxants like mivacurium and pancuronium bromide; antiparkinson agents like benstropine, trihexylphenadate, selegiline, dopamine and pergolide mesylate; hormones like estradiol, estrone, progesterone, ethinyl estradiol, medroxyprogesterone, melatonin, and octreotide acetate; and antibiotics like penicillin G, ticarcillin, tobramycin, erythromycin, gentamicin, moxalactam, cephadrine, and chloramphenicol.

As used herein, a nutritional supplement is defined as any substance that is administered as a dietary supplement to a subject. Any form of nutritional supplement that is capable of being entrapped in or bound to the lipid vesicle can be included in the preparations of the present invention. Such supplements can be purified vitamins or minerals, herbs, or plant extracts. The preferred nutritional supplements are extracts of plants, particularly herbal plants. Examples of such nutritional supplements include, but are not limited to, *Ginkgo biloba* extract, Kava Kava extract, Ginseng extract, Saw Palmetto extract, glucosamine sulfate, chromium picolinate, Milk thistle extract, Grape seed extract, Ma Huang extract, Co-Q10 supplement,water soluble vitamens such as vitamin C niacin, vitamin B1 and vitamen B12, and fat soluble vitamens such as vitamens A, D, E, and K. In the Examples that follow, the formulation of melatonin, Kava Kava, Echinecia, and Co-enzyme Q10 is described. Nutritional supplements include those both water soluble and those that are fat soluble. Such active ingredients can be delivered as single agents, combinations of agents and combinations that might incorporate other desirable biologically active materials.

It generally is contemplated that the lipid encapsulated agents according to the present invention can be administered in a variety of aerosol or pump spray administration devices, such as pump actuated sprayers, atomizers and nebulizers that are known to those in the art. Additionally, a wide variety of flavor ingredients can be incorporated into the formulations. The particular nonliposomal ingredients are not important so long as they do not excessively impair either the stability or bioavailability of the active ingredients contained within or associated with the lipid vesicle or liposome. Also, products such as the $CoQ_{10}$ formulation can be administered multiple times during the day in order to maintain an even dosing regimen in which blood levels remain relatively more steady than would otherwise be the case. Modifications to the formulations including the particular type of lipid/agent preparation to be utilized can be varied and optimized by those skilled in the art according to conventional techniques.

The liposomal preparation itself can contain different types of liposomes, including small unilamellar vesicles, large unilamellar vesicles, multilamellar vesicles or oligolamellar vesicles. Additionally, a combination of such lipid encapsulation forms may be used in a range that can vary from about 20 mn to 10 microns. Notably, the encapsulated material itself need not be 100% encapsulated, and the encapsulation rate can vary and be optimized within a range of about 0.1% to about 100%, preferably with 70–100% encapsulated. Viscosity of the final preparation can range from that of aqueous solution such as water to the viscosity of a paste. Additionally, the lipid encapsulated formulation can be placed in a gelatin capsule or other orally available formulation with appropriate excipients and modifiers.

As used herein, an agent is said to be lipid encapsulated when the agent is present within or on the surface of a lipid sphere. This includes, for example, entrapment within an enclosed lipid monolayer or bilayer either by fusing smaller vesicles around the substance, transmission through the membrane of a formed lipid vesicle or liposome, forming the lipid vesicle or liposome within a solution containing the substance, or binding the substance to the lipid vesicle or liposome membrane itself. Such formulations are representative of those known generally in the art.

As provided above, liposomes can exist as small unilamellar vesicles (SUV), large unilamellar vesicles (LUV) or multilamellar lipid vesicles (MLV). In liposomes, the lipid bi-layers are made up mainly of phospholipids, which are amphiphilic; they have a hydrophilic head and a lipophilic tail. In aqueous solution the lipids are arranged into layers that form closed vesicles, like artificial cells. Liposomes are classified according to the numbers of lipid layers present, the size of the liposome, and the lipid composition.

The lipids used to form the lipid vesicles and liposomes in the present formulations can be naturally occurring lipids, synthetically made lipids or lipids that are semisynthetic. Any of the art known lipid or lipid like substances can be used to generate the compositions of the present invention. These include, but are not limited to, lecithin, ceramides, phosphatidylethanolamine, phosphotidylcholine, phosphatidylserine, cardiolipin and the like. Such lipid components for the preparation of lipid vesicles are well known in the art, for example see U.S. Pat. No. 4,485,954, and "Liposome Technology", 2nd Ed, Vol. I (1993) G. Gregoriadis ed., CRC Press, Boca Raton, Fla.

The choice of the types and ratios of lipids used will be based on the delivery properties desired, the agent, the type of lipid encapsulation sought, and the method used to lipid encapsulate the agent. Because the compositions of the present invention are intended for sublingual, buccal and throat absorption or retention or absorbtion from the nasal cavity, the preferred lipids will be of the type that facilitate rapid absorption across mucus membranes within the oral or nasal cavities, are stable at room temperature and are readily formulated for aerosol or spray delivery. Lipids with these properties that are particularly preferred in the present formulations include phospholipids, particularly highly purified, unhydrogenated lecithin containing high concentrations of phosphotidylcholine, such as that available under the trade name Phospholipon 90 from American Lecithin, or Nattermann Phospholipid, 33 Turner Road, Danbury, Conn. 06813-1908.

The lipid encapsulated compositions of the present invention are made using techniques known in the art for generating liposomes and lipid vesicles. Such methods include, but are not limited to, thin lipid hydration by mechanical methods such as by vortexing or shaking, organic solvent replacement by aqueous media, formation of lipid-detergent mixed micelles followed by detergent removal, size transformation and fusion, and pH adjustment. A review of a variety of such methods is provided by Anselm et al. *Liposome Technology*, Gregoriadis, G. (ed) CRC Press, Boca Raton (1992), Bangham A.D., *Techniques in Lipid and Membrane biochemistry part II. Techniques in Life Sciences.* Hesketh et al, (eds). Elsevier Biomedical, Ireland (1982), Lasic, DO, *Biochem. J.* 256:1–11 (1988), Lichtenburg et al, *Methods of Biochem. Anal.* 33:3317462(1980) and U.S. Pat. Nos. 4,311,712, 4,485,054, 4,761,288, and 4,937,078. All patent references and other published documents identified in this specification are hereby incorporated by reference in their entirety.

In the Examples that follow, liposomes were formed using solvent drying/replacement in combination with mechanical agitation during hydration.

As is generally known, a variety of liposome and lipid vesicle types can be generated by varying the specific lipid mixtures/ratios and the methods used in generating the liposomes or lipid vesicle. For example, the lipid vesicle may be formed as a micelle whereas the liposome may be formed as a (1) multilamellar lipid vesicle (MLV) which is composed of a number of bimolecular lamellae interspersed with an aqueous medium, (2) unilamellar lipid vesicle which is composed of a single spherical lipid bilayer entrapping aqueous solution, and/or (3) multivesicular lipid vesicle that is composed of a number of vesicles. The preferred compositions will be comprised predominantly of liposomes.

As noted above, the lipid encapsulated compositions of the present invention can be either a mixture of a variety of types and sizes of liposomes and lipid vesicles or can be compositions containing one or more predominant types and sizes. For the latter types of compositions, a variety of methods are available for separating the liposomes formed into groups based on size and type. These include, but are not limited to, separation using sedimentation, gel filtration, or extrusion through straight pored filters. To make compositions which contain a mixture of liposomal types or sizes, after liposome formation, procedures for separation of the liposome into size/type groups are not employed.

The compositions of the present invention are intended to be formulated for administration as an aerosol or spray. As used herein, an aerosol or spray is defined as a liquid aerosol or spray having a liquid droplet size in a range from about 1 to 200 $\mu$m. These include coarse sprays, colloidal suspensions of liquid droplets in a gaseous carrier such as oxygen, nitrogen or a hydrocarbon propellant, and temporary suspensions of liquid droplets in the carrier.

A variety of devices are currently available that allow for the efficient delivery of liquid compositions as an aerosol or spray. Such devices include, but are not limited to, pump actuated devices and pressurized devices (liquefied gas systems, compressed gas systems, and separate propellant/concentrate systems), Sciarra, J. p. 1644 (Remington's *Pharmaceutical Sciences,* 15th Ed., Hoover, J. E., ed. Easton Pa. 1975). Examples of commercially available aerosol delivery devices include the Sprayette IV (Calmar Dispensing Systems, Inc.). The most preferred devices of the present invention, based on cost and delivery factors, are mechanical pump devices.

In addition to containing a lipid encapsulated agent, the compositions of the present invention can further include one or more additional ingredients, including, but not limited to sweeteners, like corn syrup, honey, sorbitol, sugar, saccharin, stevia or aspartame, and buffers. like sodium hydroxide, hydrochloric acid and potassium phosphate, caffeine, citric acid, hydroxy citric acid.

The components of a formulation of the present invention may further include purified soy or egg lecithin in concentrations from about 0.10 to 50%, cholesterol or another zoosterol or phytosterols in concentrations from about 0.001 to 5%, tocopherol and/or another antioxidant like ascorbal palmitate and/or BHA and/or BHT in concentrations from about 0.01 to 3%, glycerin or propylene glycol or butylene glycol in concentrations from about 0.1 to 20%, ethanol or isopropyl alcohol or SD alcohol in concentrations from about 0.1% to 10%, benzyl alcohol or other preservatives such as sodium benzoate or potassium sorbate or citrus seed extract, in concentrations from about 0.015 to 4%, vitamins, nutritional supplements, hormones, plant extracts, drugs, or other biologically active ingredients in concentrations from about 0.001 to 99.9%, flavor or other taste masking ingredients, such as natural peppermint oil, menthol, synthetic strawberry flavor, orange flavor, chocolate, vanilla flavoring in concentrations from about 0.01 to 10%, a solubilize or surfactant, such as polysorbate 20 or polysorbate 80 in concentrations of about 0.01%, and purified water from about 2% to 99.9%.

The minimum ingredients of which the compositions of the present invention are comprised include from about 5–99.9% purified water; from about 0.1–50% purified phospholipid; from about 0.001–90% active ingredient; from about 1–15% solvent, if needed; and from about 0.05–5% preservative.

The lipid/agent delivery system of the present invention is unexpectedly beneficial because it is non-invasive and the lipid encapsulation and aerosol or spray administration of an aqueous solution provides enhanced absorption properties of the agent. The lipid encapsulated sprays or aerosols of the present invention are intended to provide from about a 20 to 100% increase in the bioavailability of an agent when compared to solid administered forms. More preferably, the composition will provide from about a 30% to 50% increase in bioavailability of the agent over an extended period of time, in comparison with comparable doses delivered to the gastrointestinal tract, e.g., by tablet.

The present invention further provides methods for administering agents to a subject, which comprises orally or nasally administering, as an aerosol or spray, a lipid encapsulated agent as herein described. Additionally, this method provides a route of delivery that can improve compliance.

Any subject can be administered the compositions of the present invention. Such subjects include humans as well as other mammalian organisms or birds and lizards. Agents, such as nutritional supplements, are becoming components in the diets of domesticated mammals such as pets and livestock.

When administered, the compositions of the present inventions optimally are held in the oral cavity for a period of time sufficient for absorption of the agent sublingually. The period of time needed to obtain absorption will vary based mainly on the type of lipid particle, the lipids that make up the lipid coat, the agent encapsulated, and delivery system used. A skilled artisan can readily determine the time needed to achieve, e.g., sublingual absorption and vary these parameters to optimize delivery for a given product. Alternatively, the composition of the present invention is administered to the nasal cavity for subsequent local effectiveness or for systemic activity.

In the Examples that follow, a lipid encapsulated melatonin spray was found to provide approximately a 33% increase in bioavailability of melatonin, over an eight hour period, when compared to orally administered melatonin in tablet form. In addition, drowsiness was noted ½ hour after administration of the lipid encapsulated spray while only a single yawn was noted 4 hours after administration of the tablet form.

The following examples are intended to illustrate, but not limit, the present invention.

Example 1
Liposomal Melatonin Spray-Formula #1

|  | % w/w |
|---|---|
| Purified Lecithin (Phospholipon 90) | 2.00 |
| Cholesterol | 0.20 |
| Tocopherol Acetate | 0.40 |
| Melatonin | 0.22 |
| Pyridoxine HCL | 0.05 |
| Glycerin | 7.50 |
| Ethyl Alcohol | 1.00 |
| Sodium Benzoate | 0.15 |
| Polysorbate 20 | 1.00 |
| Flavor | 1.00 |
| Citric Acid | 0.15 |
| Spevia/nat. sweet | 0.25 |
| Citrus seed extract | 0.05 |
| Purified Water, USP, | qs. ad. |

Components lecithin, ethyl alcohol, tocopherol acetate cholesterol and glycerin were commingled in a large volume flask and set aside for compounding.

Melatonin was added to a measured amount of the foregoing mixture and the mix was heated to 55° C. while mixing.

In a separate beaker, water, pyridoxine, sodium benzoate, polysorbate 20, and citric acid were mixed and heated to 50° C.

The water mixture was added to the melatonin mixture while vigorously mixing with a high speed, high shear homogenizing mixer at 750–1500 rpm for 30 minutes.

The homogenizer was stopped and the solution was placed on a magnetic plate, covered with parafilm and mixed with a magnetic stir bar until cooled to room temperature. Flavor and citrus seed extract were added and the solution was placed in appropriate spray dispenser.

Analysis of the preparation under an optical light microscope with polarized light at 400 X magnification confirmed the presence of both multilamellar lipid vesicles (MLV) and unilamellar lipid vesicles.

A study was conducted to compare similar doses of melatonin (3 mg) using different routes of administration. A 3 mg oral melatonin tablet was compared to a liposomal encapsulated melatonin spray which was administered sublingually using a pump sprayer.

The study was conducted under physician supervision. Day-time blood sample collection (8:00 A.M.) with reduced artificial lighting when possible were obtained over an 8 hour period. Blood specimens were then certified plasma (serum) separated and immediately frozen. This was done on a precise schedule in a dark environment for both experimental doses of melatonin. Blood samples were analyzed by radioimmunoassay (RIA) for detection of melatonin concentration.

On the day of experimentation Baseline "0" melatonin levels were drawn. Two sprays of melatonin liposome spray formula was applied to sublingual area of the mouth. Saliva was allowed to accumulate for several minutes and then swallowed. Blood samples were drawn at ½ hour, 1 hour, 1½ hours, 2 hours, 4 hours, 6 hours and 8 hours.

After 1 week (to insure a proper wash-out of melatonin spray, the same sequence and procedure was performed for the 3 mg oral melatonin tablet. All samples were sent to a certified reference laboratory after carefully packing in dry ice and sent by over night express mail to insure proper handling and radioimmunoassay (RIA) evaluations.

| | Subjects Notes & Observations |
|---|---|
| Liposomal Spray of melatonin | |
| Sample "0" Baseline | spray bottles shaken several times and primed for usage. Two sprays were applied under the tongue, held sublingually, and then swallowed after 2 minutes. |
| Sample (1) - ½ hour Blood drawn | drowsiness noted, relaxation starting- no real urge to sleep, good tranquil effect. |
| Sample (2) - 1 hour | tranquillity and relaxation more pronounced; no feeling of drowsiness or vertigo. |
| Sample (3) - 1¼ hour | ability to concentrate more evident; last food intake 3 hours. |
| Sample (4) - 2 hours | no difficulties - 3–4 times yawning but no dozing. |
| Sample (5) - 4 hours | considerable yawning; no dizziness or somnolence. |
| Sample (6) - 6 hours | no serious effects, no further yawning, drowsiness is less. Driving car and performing routine tasks- no problem. |
| Sample (7) - 8 hours | no significant effect. |
| Oral Tablet 3.0 mg melatonin | |
| Sample (1) - ½ hour | no effect |
| Sample (2) - 1 hour | no effect |
| Sample (3) - 1½ hour | no effect |
| Sample (4) - 2 hours | no effect |
| Sample (5) - 4 hours | yawned 1 time while driving to lunch |
| Sample (6) - 6 hours | no effect |
| Sample (7) - 8 hours | no effect |

| Test | Result | Adult Reference Range |
|---|---|---|
| Melatonin (Plasma) | | Dark Cycle: 20–80 pg/ml |
| Sample 0 Baseline | 39.5 pg/ml | |
| Sample 1 0.5 hours | 268 pg/ml | |
| Sample 2 1 hour | 324 pg/ml | |
| Sample 3 1.5 hours | 335 pg/ml | Daytime or bright light levels may drop to less than 12 pg/ml. |
| Sample 4 2 hours | 195 pg/ml | |
| Sample 5 4 hours | 276 pg/ml | |
| Sample 6 6 hours | 341 pg/ml | |
| Sample 7 8 hours | 204 pg/ml | |
| Melatonin (Plasma) | | Dark Cycles: 20–80 pg/ml |

| | Tab | SL | |
|---|---|---|---|
| Sample 0 Baseline | 39.5 | 53.9 pg/ml | |
| Sample 1 0.5 hours | 268 | 314 pg/ml | Daytime or bright light levels may drop to less than 12 pg/ml |
| Sample 2 1 hour | 324 | 218 pg/ml | |
| Sample 3 1.5 hours | 335 | 352 pg/ml | |
| Sample 4 2 hours | 195 | 428 pg/ml | |
| Sample 5 4 hours | 276 | 362 pg/ml | |
| Sample 6 6 hours | 341 | 376 pg/ml | |
| Sample 7 8 hours | 204 | 417 pg/ml | |

Absolute Bioavailability of Melatonin Liposomal Spray

| Time Hours | Blood Concentration pg/ml | Time Interval (hours) | Avg. Conc. pg/ml | Area pgXhours/ml |
|---|---|---|---|---|
| 0.0 | 53.9 | 0 | | |
| 0.5 | 314 | 0.5 | 91.97 | 91.97 |
| 1.0 | 218 | 0.5 | 133 | 133 |
| 1.5 | 352 | 0.5 | 142.5 | 142.5 |
| 2.0 | 428 | 0.5 | 195 | 195 |
| 4.0 | 362 | 2.0 | 790 | 790 |
| 6.0 | 376 | 2.0 | 738 | 738 |
| 8.0 | 417 | 2.0 | 793 | 793 |
| | | | Total Area | 2883.5 |

Absolute Bioavailability of Melatonin Oral Tablet

| Time Hours | Blood Concentration pg/ml | Time Interval (hours) | Avg. Conc. pg/ml | Area pgXhours/ml |
|---|---|---|---|---|
| 0.0 | 39.5 | 0 | | |
| 0.5 | 268 | 0.5 | 76.87 | 76.87 |
| 1.0 | 324 | 0.5 | 148 | 148 |
| 1.5 | 335 | 0.5 | 164.75 | 164.75 |
| 2.0 | 195 | 0.5 | 132.5 | 132.5 |
| 4.0 | 276 | 2.0 | 471 | 471 |

-continued

Absolute Bioavailability of Melatonin Oral Tablet

| Time Hours | Blood Concentration pg/ml | Time Interval (hours) | Avg. Conc. pg/ml | Area pgXhours/ml |
|---|---|---|---|---|
| 6.0 | 341 | 2.0 | 617 | 617 |
| 8.0 | 204 | 2.0 | 545 | 545 |
|  |  |  | Total Area | 2155.12 |

This study demonstrates therapeutic efficiency by exploring new methods of drug administration and delivery using a liposome spray. This method of spray is unique due to the rapid absorption of the active ingredients, with a longer duration of effect because of transport via the internal jugular vein and into the systemic circulation as well as continued site of absorption. This method is far superior to orally administered tablet medication which depends upon absorption from the gastrointestinal tract, transport through the intestinal mucosa, into the hepatic-portal vein, into and through the liver and into the blood stream.

Liposomal encapsulated melatonin provided an increase of approximately 25% in bioavailability when compared to orally administered solid tablets. The lipid encapsulated spray further decreased the time necessary to achieve a serum concentration sufficient to induce drowsiness. While the orally administered melatonin tablet was found associated with a yawn 4 hours after administration, the lipid encapsulated spray was associated with drowsiness ½ hour after administration.

It is suggested that, because of low toxicity of melatonin, if sleep is not induced within 10–15 minutes, a spray application can be repeated with excellent results.

Example 2
Liposomal Appetite Suppressant Spray

|  | % w/w |
|---|---|
| Lecithin (Phospholipon 90) | 2.00 |
| Tocopherol Acetate | 0.40 |
| Hydroxy Citric Acid (50%) | 25.00 |
| Glycerin | 5.00 |
| Ethyl Alcohol | 1.25 |
| Polysorbate 20 | 3.00 |
| Chromium Picolinate | 0.025 |
| Citru seed extract | 0.05 |
| $K^+$ sorbate | 0.10 |
| $Na^+$ benzoate | 0.15 |
| Nat. sweetener | 0.25 |
| Purified Water, USP | qs. ad. |

Components lecithin, ethyl alcohol, tocopherol acetate cholesterol and glycerin were commingled in a large volume flask and set aside for compounding.

In a separate beaker, water, hydroxy citric acid, glycerin, polysorbate 20, chromium picolinate were mixed and heated to 50° C.

The water mixture was added to the lipid mixture while vigorously mixing with a high speed, high shear homogenizing mixer at 750–1500 rpm for 30 minutes.

The homogenizer was stopped and the solution was placed on a magnetic plate, covered with parafilm and mixed with a magnetic stir bar until cooled to room temperature. Flavor and citrus seed extract were added and the solution was placed in appropriate spray dispenser.

The solution was placed in appropriate spray dispenser.

Analysis of the preparation under an optical light microscope with polarized light at 400 X magnification confirmed presence of both multilamellar lipid vesicles (MLV) and unilamellar lipid vesicles.

Each of the following composition were formulated as described above with the active ingredients being added to the lipid mixture of water mixture during compounding.

Example 3
PRODUCT: Kava Kava (30%) Spray

| INGREDIENTS: | % |
|---|---|
| Deionized Water | 72.17 |
| Glycerin | 12.50 |
| Polysorbate-20 | 2.00 |
| Lecithin | 1.50 |
| Ethyl Alcohol | 1.00 |
| Citrus Seed Extract | 0.50 |
| Tocopherol Acetate | 0.25 |
| Nat. Sweetener (Stevia) | 0.25 |
| Flavor (Nat. Passionfruit & Nat. Vanilla-Mint Ext.) | 0.75 |
| Potassium Sorbate | 0.10 |
| Citric Acid | 0.05 |

Example 4
PRODUCT: Echinacea Oral Spray

| INGREDIENTS: | % |
|---|---|
| Deionized Water | 74.85 |
| Glycerin | 15.00 |
| Polysorbate-20 | 2.50 |
| Lecithin | 1.50 |
| Flavor Citrus | 0.75 |
| Citrus Seed Extract | 0.50 |
| Tocopherol Acetate | 0.25 |
| Nat. Sweetener (Stevia) | 0.25 |
| Potassium Sorbate | 0.10 |
| Echinacea Purpurea Augustifolia | 4.30 |

Example 5
PRODUCT: Kava Kava Spray II

| INGREDIENTS: | % |
|---|---|
| Deionized Water | 74.85 |
| Kava Kava Extract | 5.00 |
| Echinacea Extract | 5.00 |
| Ginger Extract | 1.00 |
| Honey Clover | 10.00 |
| Lecithin | 0.50 |
| Cholesterol | 0.05 |
| Vitamin E Acetate | 0.05 |
| Propylene Glycol | 0.50 |
| Polysorbate-20 | 0.50 |
| Benzyl Alcohol | 0.50 |
| Sodium Benzoate | 0.10 |
| Potassium Sorbate | 0.10 |
| Orange #52113-26 | 2.00 |

Example 6
PRODUCT: Co-Enzyme Q10 Spray

| INGREDIENTS: | % |
|---|---|
| Deionized Water | 74.85 |
| Glycerin | 15.00 |
| Lecithin | 0.50 |
| Co-Enzyme Q10 | 4.30 |
| Polysorbate-20 | 0.50 |
| Nat. Orange Flavor | 0.75 |
| Citrus Seed Extract | 0.50 |
| Potassium Sorbate | 0.10 |
| Tocopherol Acetate | 0.25 |
| Nat. Sweetener (Stevia) | 0.25 |

We claim:

1. A liposomal composition suitable for the aerosol or spray delivery of melatonin to a subject, said composition comprising melatonin and optionally an additional supplement in phospholipid liposomes and a carrier wherein the liposomes have between about 20 nm and 10 microns in diameter and results in absorption into the blood stream, when administered, wherein the phospholipid liposome comprises one or more bilayer forming lipids, wherein said composition provides an increase in bioavailability of said supplement or drug of approximately 20 % or more when compared to an orally administered solid form, and wherein said composition comprises by weight percent, from about 0.25 to 20% lecithin, from about 0.025 to 2% cholesterol or zoosterol or phytosterol, from about 0.01 to 3% antioxidant, from about 0.05 to 0.4% melatonin, from about 0.1 to 20% glycerin, propylene glycol or butylene glycol, from about 0.1% to 10% ethanol, from about 0.015 to 4% anti microbial agent and from about 2 to 99.9% water.

2. The composition of claim 1 wherein said composition further comprises one or more additional supplements selected from the group consisting of *Ginkgo biloba* extract, Kava Kava extract, Ginseng extract, Saw Palmetto extract, glucosamine sulfate, chromium picolinate, Milk thistle extract, Grape seed extract, Ma Huang extract, Echinecia, Co-Q10 supplement, water soluble vitamins, and fat soluble vitamins.

3. The composition of claim 1, wherein said composition provides an increase in bioavailability from about 20% to 50% when compared to an orally administered solid form of said agent.

4. The composition of claim 3, wherein said composition provides an increase in bioavailability of approximately 30% when compared to an orally administered solid form of said agent.

5. A method for the systemic administration of a drug or supplement to a subject, said method comprising the steps of:

orally administering an aerosol or spray comprising the composition of claim 1 or 2 which results in said composition being sublingually absorbed into the blood stream, wherein the phospholipid vesicles comprising one or more bilayer forming lipids and said method provides an increase in bioavailability of approximately 20% or more when compared to an orally administered solid form of said supplement or drug.

6. The method of claim 5 wherein said aerosol or spray is provided by a mechanical pump delivery device.

7. The method of claim 5, wherein said method provides an increase in bioavailability from about 20% to 50% when compared to an orally administered solid form of said agent.

8. The method of claim 7, wherein said method provides an increase in bioavailability of approximately 30% when compared to an orally administered solid form of said agent.

9. A mechanical pump delivery device containing the composition of claim 1.

* * * * *